(12) United States Patent
Lemay et al.

(10) Patent No.: US 7,976,161 B2
(45) Date of Patent: Jul. 12, 2011

(54) METHOD AND SYSTEM TO ASSESS OBJECTIVELY VISUAL CHARACTERISTICS

(75) Inventors: Sebastien Lemay, Charenton le Pont (FR); Martha Hernandez, Charenton le Pont (FR); Pedro Ourives, Charenton le Pont (FR)

(73) Assignee: Essilor International (Compagnie Generale D'optique), Charenton le Pont (FR)

( * ) Notice: Subject to any disclaimer, the term of this patent is extended or adjusted under 35 U.S.C. 154(b) by 0 days.

(21) Appl. No.: 12/375,072

(22) PCT Filed: Jul. 24, 2007

(86) PCT No.: PCT/EP2007/057606
§ 371 (c)(1),
(2), (4) Date: Jan. 26, 2009

(87) PCT Pub. No.: WO2008/012299
PCT Pub. Date: Jan. 31, 2008

(65) Prior Publication Data
US 2010/0091241 A1    Apr. 15, 2010

(30) Foreign Application Priority Data
Jul. 28, 2006   (EP) .................................... 06291234

(51) Int. Cl.
*A61B 3/10* (2006.01)
*A61B 3/00* (2006.01)
(52) U.S. Cl. .......................... 351/205; 351/200; 351/221
(58) Field of Classification Search .................... 351/205
See application file for complete search history.

(56) References Cited

U.S. PATENT DOCUMENTS

| 1,351,220 | A | 8/1920 | Shigon |
| 2,337,898 | A | 12/1943 | Jobe et al. |
| 2,441,783 | A | 5/1948 | Williams |
| 2,523,007 | A | 9/1950 | Glazer |
| 2,635,502 | A | 4/1953 | Richards |
| 3,454,331 | A | 7/1969 | Maitenaz |
| 4,338,002 | A | 7/1982 | Gafert |
| 4,572,692 | A | 2/1986 | Sauber |
| 5,444,504 | A | 8/1995 | Kobayashi et al. |
| 5,859,687 | A | 1/1999 | Heine et al. |
| 5,889,577 | A | 3/1999 | Kohayakawa |
| 6,286,957 | B1 | 9/2001 | Livnat |
| 2002/0176051 | A1 | 11/2002 | Saladin |
| 2003/0143391 | A1 | 7/2003 | Lai |

(Continued)

FOREIGN PATENT DOCUMENTS
CH           545097       12/1973
(Continued)

*Primary Examiner* — Dawayne A Pinkney
(74) *Attorney, Agent, or Firm* — Occhiuti Rohlicek & Tsao LLP

(57) ABSTRACT

A method to assess objectively visual characteristics of one eye (10) of a patient (1) comprising the steps of: a) positioning the patient's (1) head in a reading position, b) determining the visual characteristics by using a device (3) arranged to assess objectively visual characteristics of the eye (10), the device being arranged to emit a light beam (81, 82). Relates also to a system for assessing objectively visual characteristics of one eye (10) of a patient (1) comprising:—a head support arranged to position the patient's (1) head in a reading position, a device (3) arranged to assess objectively visual characteristics of the eye (10), the device (3) being arranged to emit a light beam (81, 82).

14 Claims, 4 Drawing Sheets

U.S. PATENT DOCUMENTS

2009/0076602 A1 * 3/2009 Ho et al. .................. 623/6.11

FOREIGN PATENT DOCUMENTS

| DE | 7015772 | 7/1970 |
|----|---------|--------|
| EP | 1700562 | 9/2006 |
| ES | 2043546 | 12/1993 |
| FR | 2384232 | 10/1978 |
| FR | 2522264 | 9/1983 |
| FR | 2538239 | 6/1984 |
| FR | 2672792 | 8/1992 |
| GB | 12227 | 5/1913 |
| GB | 1241156 | 7/1971 |
| GB | 1269799 | 4/1972 |
| WO | WO01/62139 | 8/2001 |
| WO | WO2006/076653 | 7/2006 |

* cited by examiner

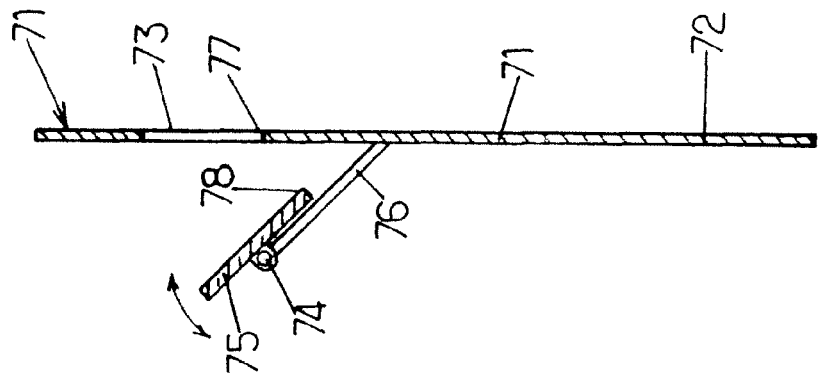
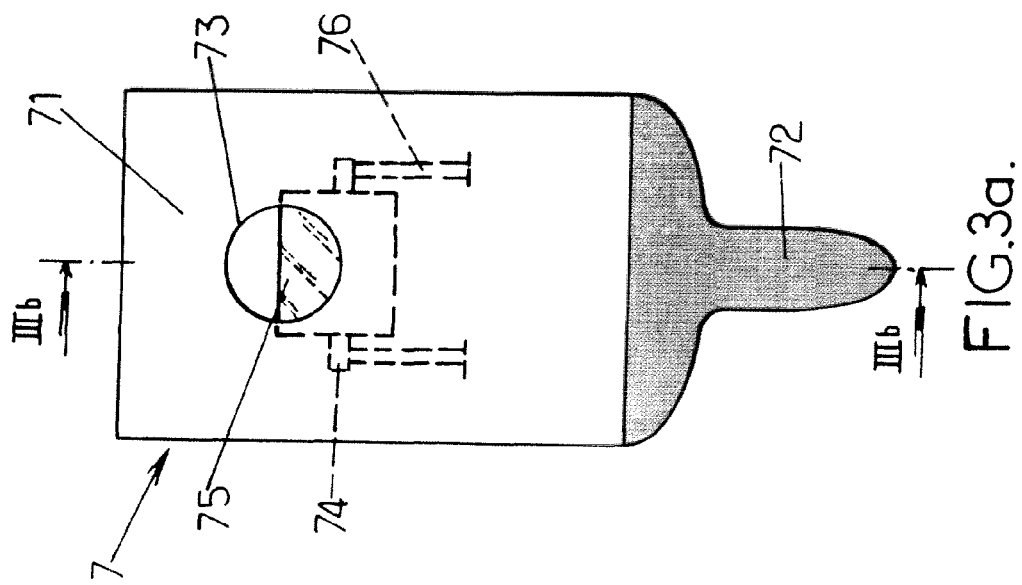

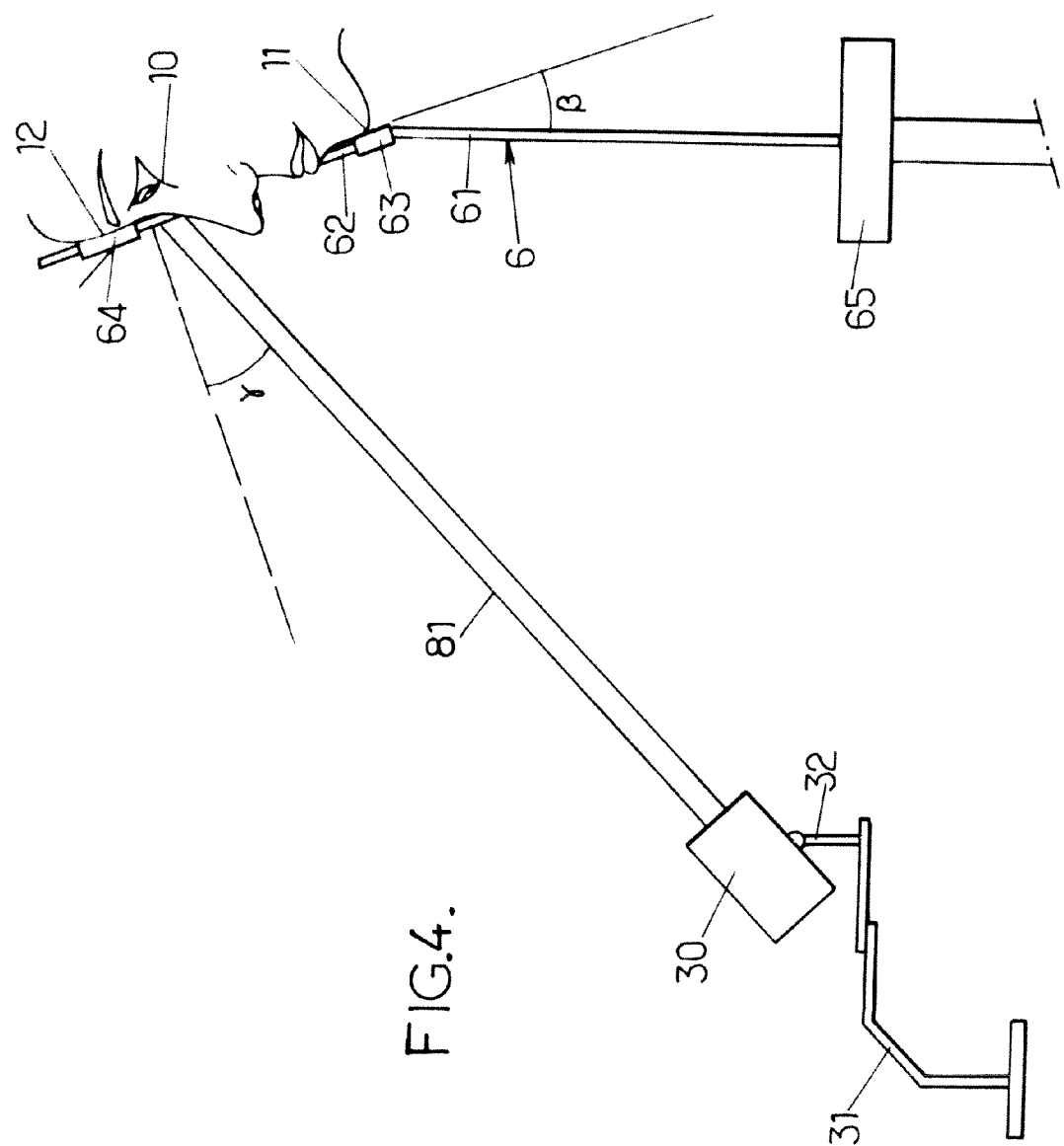

METHOD AND SYSTEM TO ASSESS OBJECTIVELY VISUAL CHARACTERISTICS

CROSS-REFERENCE TO RELATED APPLICATIONS

This application is the National Stage of International Application No. PCT/EP2007/057606, filed on Jul. 24, 2007, which claims the priority of European Application No. 06291234.0, filed on Jul. 28, 2006. The contents of both applications are hereby incorporated by reference in their entirety.

The present invention relates to a method and a system to assess objectively visual characteristics of an eye, and thus determining eye glass lenses needed to correct the defective vision. The invention relates also to an apparatus, namely a viewing board, suitable to implement said method.

The vision characteristics that can be determined with said method can be, for example, objective refractive characteristic, lag of an eye or ocular aberrations.

Objective refractive characteristic measurement is used when the refractive error of an eye is determined without input by the patient.

The patient may be required to cooperate in the placement of the head, but subjective information is not obtained from the patient about the quality of vision during the procedure.

The refractive characteristic of the eye is determined according to a set of criteria identified in advance by a human operator or programmed instrument.

Skiascopy is a form of objective refraction measurement in which the judgement of a human operator is required to determine the refractive characteristic of an eye. Such an operator is commonly known as an optometrist.

The judgement of a human operator may be replaced by the logic of an instrument, computer or both.

Refractive characteristic of an eye can also be estimated objectively by a process called photorefraction.

To measure the optical characteristics of a closed optical system, light must traverse the optical path twice and there must be some structure at the closed end of the optical path that can reverse the direction of light travel. The retina, or more accurately the ocular fundus, acts as the primary reflector that reverses the direction of light in the eye such that light emitted from the eye can be analyzed. The fundus reverses the direction of light travel through a combination of reflections occurring at refractive index inhomogeneities at surfaces or within the tissue. Specular reflections from the ocular fundus occur according to intensities derived from Fresnel's formula for specular reflection at the layered concave optical interfaces between the vitreous retina, pigment epithelium and choroid.

The technique of skiascopy is used to objectively determine the refractive status of the eye relative to the point of fixation. Skiascopy is usually the first technique performed in the ocular examination that determines the patient's refractive status, and it is usually immediately followed by the subjective refraction. The skiascopic findings, therefore, usually serve as the starting point for the subjective refraction and are independent confirmation of the subjective results. Skiascopy can be performed on infants, the mentally infirm, low-vision patients, and uncooperative or malingering patients. Thus the skiascopic findings may be heavily relied on for prescription of optical corrections when patients are unable or unwilling to give reliable subjective responses.

Commonly used synonyms of skiascopy are "retinoscopy" and "skiametry", and other synonyms occasionally seen in literature are "umbrascopy", "pupilloscopy", "retinoskiascopy".

A skiascope is a small, handheld device that emits visible white light toward the pupil of the eye being analyzed and allows the operator to view the red reflex of light reflected back through the pupil from the ocular fundus.

Typically, the skiascope has a plane reflecting surface which allows light originating from below to be reflected toward the patient's eye. The reflecting surface is perforated or half-silvered, which allows the operator to view the patient's eye through a central aperture. A divergent beam of light from a filament source is refracted by a plus condensing lens below the reflecting surface before it is reflected by the perforated or half-silvered mirror. The reflected beam is usually divergent and is directed toward the patient's pupil.

The objective of skiascopy is to find the position of the paraxial far point (punctum remotum) of the eye.

Basically, the operator views through the aperture of the skiascope at a distance of 40 to 100 cm from the patient's eye and shines the beam of the skiascope into the pupil of the patient's eye while the patient fixates a distant target.

By observation of the skiascopic pupillary reflex as the meridional axis orientation of the divergent rectangular light beam is altered, and as the rectangular beam is swept across the pupil form side to side along the two principal power meridians, the operator is able to deduce the location of the far point of each primary meridian relative to the position of the skiascope aperture through which the operator is viewing. The attributes of the pupillary reflex that signify the relative position of the far point are linked to "with" or "against" motions: "with" motion of the pupillary streak reflex, compared with movement of the incident divergent rectangular beam, indicates a far-point location behind the skiascope aperture, in the continuum between the operator and infinity (slightly myopic and emmetropic eyes) or behind the eye (hyperopic eyes). "Against" motion of the streak indicates a far-point location between the skiascope aperture and the patient's eye (moderately to highly myopic eyes).

To determine the correction, trial lenses, trial frames, and refractors are used. The far point of the eye is moved to the position of the skiascope aperture by placement of lenses at the spectacle plane having the eyes approximate refractive correction.

Commonly used skiascopes are of "Heine type" as disclosed for example in patent documents GB 1 269 799 or in U.S. Pat. No. 5,859,687.

A schematic diagrammatic view of commonly used skiascopic method is shown on FIG. 1.

The patient's 1 eye 10 is positioned to face an eye of an operator 2. A viewing board 4 is disposed between the patient 1 and operator 2. The eye 10 of the patient is focused on said viewing board 4, where a scene, for example a text, is printed on. Viewing board comprises a hole, where the incident and reflected beam 8 can pass through.

Skiascope 3 is used to generate incident beam and measure the characteristics of the reflected beam. The head of the patient can be placed against a head support 5 to maintain the eye at a precise position. A commonly used distance between the patient's eye 10 and the viewing board 4 is 0.40 m.

Refractive characteristic of eye 10 is then objectively assessed following preceding method.

The "lag" is another visual characteristic which is useful to measure and may be determined by using skiascopy, for example heterodynamic skiascopy. The "lag" is defined as being the lag of accommodation and relates the distance between where the eye should be focused (for example a book when reading) and the "resting point of accommodation" (RPA) which is where the eye naturally focus when it has nothing to focus on. RPA varies from person to person.

Effects of lag of accommodation are for example described in chapter 4 of the book "Ocular accommodation, convergence, and fixation disparity—A Manuel of Clinical Analysis" (Second Edition) which is well known in the optometry field.

Measurement method of the lag of accommodation is described on pages 137 to 141 of the same book. Briefly, "standard" measurement of lag is done when modifying the position of the skiascope by the operator up to a distance where there is no ocular reflection movement, and when the patient's eye faces the skiascope, as shown in FIG. 1.

Even though these methods, called later on the "standard" methods, are widely used, there is still a need for an improved method to assess objectively refractive and/or lag characteristic of an eye of a patient.

The inventors have observed that the refractive and/or lag characteristic determined with the standard methods may be non representative of the accurate correction to be determined.

The inventors have identified that the discrepancy between the standard method results and the accurate correction for a viewer may reach a significant level when the viewer is in a reading position.

This observation is of great importance, for example when the patient needs to wear presbyopia corrective glasses, such as monofocal lenses or progressive addition lenses (PAL).

PAL have gained worldwide acceptance as the most performant ophthalmic lenses for correction of presbyopia because they provide comfortable vision at all distances.

The wording "a reading position" is widely used for a man skilled in the art of vision correction and has to be understood as a reading position where the object to be read is situated between 25 to 50 cm from the eye or more generally from spectacles plan of the reader (see for example: "Le nouveau Dictionnaire de la vision"—Michel Millodot—Médiacom Vision Editeur).

As for an example, the reading position is the Harmon distance which is defined as being the optimal working distance where the physiological energy of the reading position corresponds to a minimum.

According to Harmon (publications dated 1951 and 1958) this position is determined when the head and the trunk are maintained in a minimum muscular activity, then reducing the tensions.

Boivin (publication dated 1975) has studied the Harmon position and suggested following criteria:
- The face plane is parallel to the working plane of the element to be read and the back is tilted ahead with an angle of about 20°.
- The distance between the working plane and the eye on the spectacles plane is approximately the distance between the elbow and the middle finger joint. This distance is usually called the Harmon distance.
- The lines corresponding to the projection of the eyes on the working plane are part of an isosceles triangle when the fixation point is in a median body plane.
- Linear eyes movements are not more than plus and minus 20° from here and there the median body plane.

It has to be understood that a "reading position" according to the present invention is such a reading position and is not an intermediate or far vision reading position, such as for example when watching a computer screen or reading an advertisement.

Thus the goal of the present invention is to improve the method and system used to assess objectively visual characteristic of one eye of a patient in particular when the patient needs to wear presbyopia corrective glasses.

This object is obtained according to the invention by a method to assess objectively visual characteristics of one eye of a patient comprising the steps of:
  a) positioning the patient's head in a reading position,
  b) determining the visual characteristics by using a device arranged to assess objectively visual characteristics of the eye, the device being arranged to emit a light beam.

The visual characteristics objectively assessment of the two eyes of a patient can be done successively eye by eye or simultaneously, but it has to be understood that the measured characteristics are specific of each eye by himself. It has then to be understood that the visual characteristics of the present invention are not binocularly characteristics.

The device arranged to assess objectively visual characteristics of one eye can be, for example, a skiascope used to assess the refractive and/or lag characteristic. The light beam emitted by the skiascope can be advantageously reflected by a mirror in order to improve operator's comfort. Advantageously, the mirror is substantially horizontal.

The patient's head can be orientated in any position, for example the axis of the head, from neck to head crown, is in a vertical or a horizontal position, or in a tilted position (bowed head).

Following an embodiment, the patient's head is tilted of an angle $\beta$ and $\beta$ is between 10° and 40°, for example more than or equal to 15°, and/or less than or equal to 30°.

The angle $\beta$ is defined as the angle between the axis of the chest of the patient and his head position (referred as the axis of the head, from neck to head crown). When the patient is sitting, his chest is substantially vertical.

The patient's eye can be orientated in any position, for example the direction his eye is looking at is vertical, horizontal position, or tilted.

According to an embodiment, the patient's eye is tilted of an angle $\gamma$ and $\gamma$ is between 10° and 40°, for example more than or equal to 15°, and/or less than or equal to 30°.

The angle $\gamma$ is defined as the angle between the perpendicular to the head position of the patient and the direction his eye is looking at, referred as the viewing position.

The angle $\gamma$ can also be close to 0° and the viewing position then is substantially perpendicular to the head position of the patient.

Following an embodiment, the determination of the refractive and/or lag characteristic is performed when the patient is viewing a scene and where the light beam passes through said scene.

The scene may also be plane and for example horizontal ($\delta$ close to 0°) or vertical ($\delta$ close to 90°) or tilted.

According to previous embodiment, the scene may be plane, and tilted of an angle $\delta$, and $\delta$ is between 30° and 50°, for example more than or equal to 35° and/or less than or equal to 45°.

The angle $\delta$ is defined as the angle between the scene plane and a horizontal line.

Preferred parameters have been determined when testing the visual behaviour of a population of patients. A significant part of them are presbyopes. Preferred head, eye direction, scene position have been observed and optimum parameters are identified to implement the method.

The invention also related to a system for assessing objectively visual characteristics of one eye of a patient comprising:

a head support arranged to position the patient's head in a reading position, a device arranged to assess objectively visual characteristics of the eye, the device being arranged to emit a light beam.

The device can be, for example, a skiascope used to assess objectively refractive and/or lag characteristic of the eye of a patient comprising. In this case, the system further comprises:

an inclined scene support arranged to be substantially perpendicular to the patient's viewing direction; and a mirror situated on a light path between the skiascope and the patient's head.

According to an embodiment of the system, the mirror is substantially horizontal.

The device can also be an aberrometer arranged to assess objectively the ocular aberration of one eye. In this case the system further comprises:

a support arranged to vertically adjust the head support; and a mobile assembly arranged to tilt the aberrometer so that the light beam can be directed to the eye.

The invention also relates to a viewing board suitable to implement the here above mentioned method to assess objectively visual characteristics of one eye. The viewing board comprises a hole and a tiltable mirror where the tiltable mirror is hinged with the viewing board so as to be in a substantially horizontal position when tilting the viewing board.

According to an embodiment, the tilting axis of the tiltable mirror is arranged so as to substantially include the centre of gravity of the tiltable mirror.

Following to an embodiment, an edge of said mirror can be located close to an edge of said hole.

According to an embodiment, the viewing board is plane and a text is written on it.

Following to an embodiment, the viewing board is a two parts board comprising a first part with a scene and said hole and a second part which is a handle.

The invention is further described in the detailed description of non limiting embodiments as depicted and explained below.

In the drawings:

FIG. 3 shows a diagrammatic view (frontal view FIG. 3a and longitudinal section view FIG. 3b) of a viewing board according to the invention; and FIG. 4 shows a diagrammatic view of implementing a method according to the invention.

Figure 1:
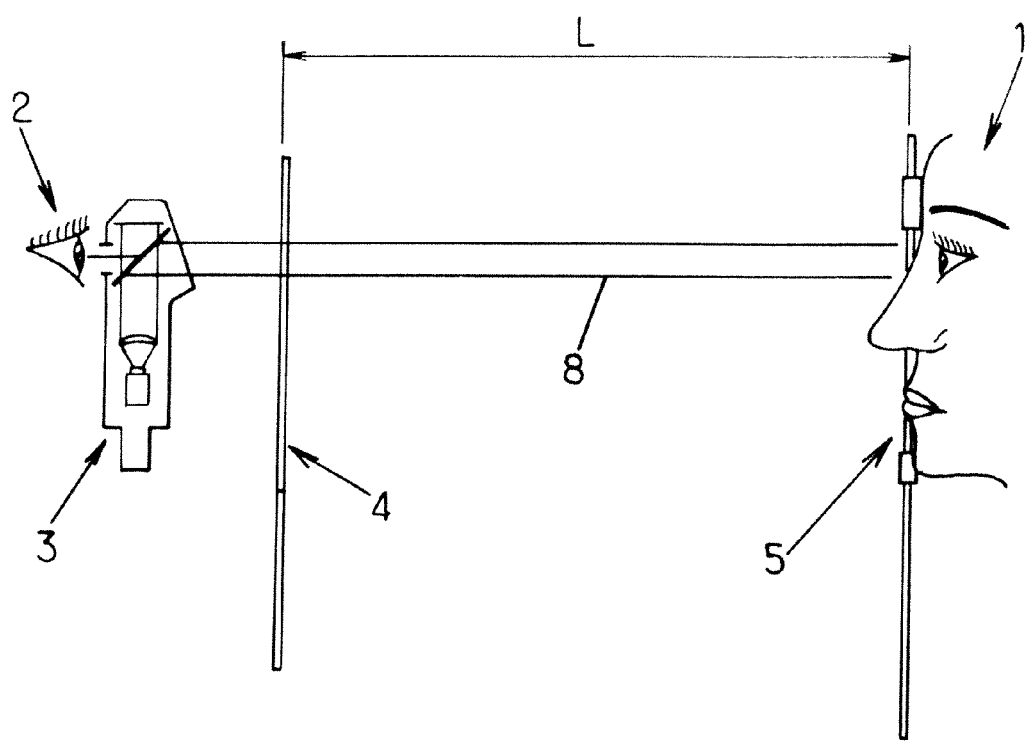
FIG. 1 shows a diagrammatic view of implementing the "standard" method.
Figure 2:
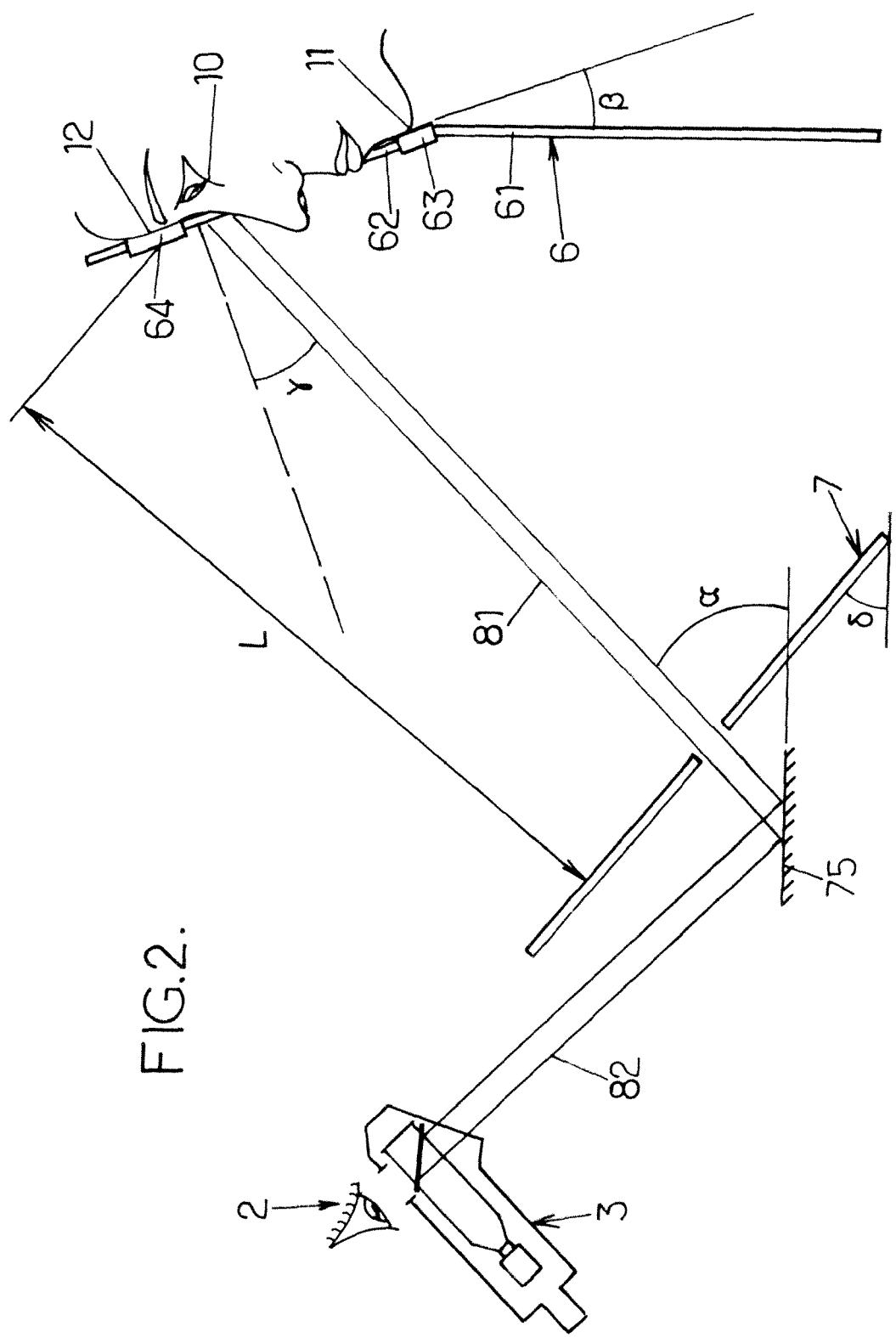
FIG. 2 shows a diagrammatic view of implementing a method according to the invention.

According to the present invention, as illustrated in FIG. 2, the patient 1 eye 10 does not look at the eye of the operator 2, but looks at the viewing board 7 so that the patient 1 is in a reading position.

The patient 1 is sitting and his chest is vertical.

The head of the patient 1 is tilted, for example, by an angle β equal to 25°. The eye 10 of the patient 1 is looking at the viewing board 7 following a tilted viewing direction. Said viewing direction is, for example, tilted by an angle γ equal to 20°.

As a result, the light beam 81 corresponding to resulting patient's viewing direction is tilted by an angle α, for example equal to 45° referring to a horizontal line.

Light beam 81 is reflected by a mirror 75 to a skiascope 3 following light beam 82. Operator 2 observes the patient's eye 10 through said skiascope. As explained above, the skiascope emits light and is used to determine objectively refractive and/or lag characteristic of the eye.

Viewing board 7 is tilted, for example, to be substantially perpendicular to patient's viewing direction. Viewing board is for example tilted by an angle δ equal to 40° referring to a horizontal line.

Mirror 75 is arranged behind viewing board 7, on the operator's side. Mirror 75 is substantially horizontal, but could also be tilted if the operator's viewing conditions need it.

A head support 6 is provided to position the head of patient in operating condition.

Head support 6 comprises two parts, a vertical part 61 and a tiltable part 62.

The chin 11 of the patient 1 is placed on a chin support 63 and the forehead 12 of the patient 1 is placed on a forehead support 64. It is thus possible to observe the patient eye in a fixed position, said position being arranged to be a reading position so that his eye 10 is focusing the viewing board 7.

The length L between the eye 10 of the patient 1 and the viewing board is preferably 0.40 m. It is for example a Hartman distance.

A viewing board 7 according to the invention is shown on FIG. 3. FIG. 3a is a frontal view where FIG. 3b is a longitudinal section view according to line IIIb-IIIb. Viewing board 7 is a plane board with a circular hole 73. A first part 71 is larger than a second part 72. Second part 72 is a handle and first part 71 comprises the hole 73 and a scene, for example a written text, arranged around the hole 73. A mirror 75 is part of said viewing board 7 and arrange so as to be in optical connexion with the hole 73. By "optical connexion" is meant that a light beam can pass through the hole 73 and be reflected by mirror 75. Mirror 75 is tiltable around a tilting axis 74. The tilting axis 74 is situated behind a face of first part 71, and shifted from a few centimetres from said face. A part 76 attaches the axis 74 to first part 71. The size of mirror 75 and the position of axis 74 are arranged so that an edge 78 of the mirror 75 is close (shifted from a few millimetres) to an edge 77 of the hole 73, when the viewing board 7 is tilted by an angle of 40 to 60° referring to an horizontal line.

The center of gravity of the mirror 75 is situated very close to the tilting axis 74 of the mirror and can for example be situated on this tilting axis.

For example, the circular hole 73 has a diameter of 1.5 cm, the length of the main side of the first part 72 is 22 cm and its width is 14 cm. The distance between the hole 73 centre and the bottom part of first part 72 is 16 cm. Handle 72 is designed to be comfortable when hold by the patient.

The patient 1 can hold said viewing board 7 and tilt it to be in a comfortable reading position. As mirror 75 is tiltable, so as it remains in a substantially horizontal position, operator 2 can watch the patient's eye in a wide range of tilting angle of the viewing board.

Operator 2 can then determine accurately the refractive and/or lag characteristic of the patient's 1 eye 10.

The detailed description hereinbefore with reference to the drawings illustrates a method to assess objectively visual characteristics of one eye (10) of a patient (1). The method comprises the steps of:

a) positioning the patient's (1) head in a reading position; and b) determining the visual characteristics by using a device (3) arranged to assess objectively visual characteristics of the eye (10), the device being arranged to emit a light beam (81, 82).

The detailed description hereinbefore with reference to the drawings further illustrates a system for assessing objectively visual characteristics of one eye (10) of a patient (1). The system comprises:
- a head support arranged to position the patient's (1) head in a reading position; and
- a device (3) arranged to assess objectively visual characteristics of the eye (10), the device (3) being arranged to emit a light beam (81, 82).

The detailed description hereinbefore with reference to the drawings further illustrates a viewing board (7) comprising a hole (73) and a mirror (75) which are arranged to be optically connected.

The aforementioned characteristics can be implemented in numerous different manners. In order to illustrate this, some alternatives are briefly indicated.

In the above-mentioned detailed description, the visual characteristics are objective refractive characteristics or lag of an eye. It has to be understood that it can be any other visual characteristics of an eye like, for example, but not limited to, ocular aberrations or the curvature of the anterior surface of the cornea.

In the above-mentioned detailed description the device (3) arranged to assess objectively visual characteristics of one eye, was a skiascope used to assess the refractive and/or lag characteristics of one eye (10).

But the device (3) can also be, for example, an aberrometer (30) arranged to assess objectively the ocular aberration of one eye. The aberrometer can be, for example, a Shack-Hartmann aberrometer, in particular the aberrometer IRIX 3 of the Imagine Eyes Company.

As illustrated in FIG. 4, the aberrometer (30) is placed on a mobile assembly (31, 32) arranged to tilt the aberrometer (30) by an angle α, for example, of 45° referring to a horizontal line, in order to be able to assess ocular aberration with a 45° lowering of the viewing direction compared to the horizontal line. In this case, the head of the patient is tilted by an angle β equal to 25° and the viewing direction is tilted by an angle γ equal to 20°. The head support (6) is advantageously placed on a support (65) arranged to vertically adjust the head support (6).

The device (30) can also be a keratometer, also known as a ophthalmometer, in order to assess another visual characteristic, i.e. the curvature of the anterior surface of the cornea. More generally, the device (3) can be any device arranged to objectively assess visual characteristic of one eye The remarks made herein before demonstrate that the detailed description with reference to the drawings, illustrate rather than limit the invention. There are numerous alternatives, which fall within the scope of the appended claims. Any reference sign in a claim should not be construed as limiting the claim. The word "comprising" does not exclude the presence of other elements or steps than those listed in a claim. The word "a" or "an" preceding an element or step does not exclude the presence of a plurality of such elements or steps.

The invention claimed is:

1. A method to assess objectively a refractive characteristic and/or a lag characteristic of one eye of a patient comprising the steps of:
   a) positioning the patient's head in a reading position where an object to be read is situated between 25 to 50 cm from the eye or from spectacles plane of the patient and where the patient's head is tilted at an angle β, defined as the angle between the axis of the chest of the patient and the patient's head position, where β is between 10° and 40°;
   b) determining the refractive characteristic and/or the lag characteristic by using a skiascope, the skiascope being arranged to emit a light beam;
   and wherein the determination of the refractive characteristic is performed when the patient is viewing a scene and where the light beam passes through the scene, where said scene is plane, the plane being tilted at an angle δ, defined as the angle between the scene plane and a horizontal line, and δ is between 30° and 50°.

2. The method of claim 1 where the light beam is reflected by a mirror situated on a light path between the skiascope and the patient.

3. The method of claim 2 where the mirror is horizontal.

4. The method of claim 1 where the angle β is more than or equal to 15°.

5. The method of claim 1 where the angle β is less than or equal to 30°.

6. The method of claim 1 where the patient's eye is tilted at an angle γ, defined as the angle between the perpendicular to the head position of the patient and the direction his eye is looking at, referred as the viewing position, and γ is between 10° and 40°.

7. The method of claim 1 where the angle β is more than or equal to 15°.

8. The method of claim 6 where the angle β is less than or equal to 30°.

9. The method of claim 1 where the determination of a refractive characteristic is performed when the patient is viewing a scene and where the light beam passes through the scene.

10. The method of claim 1 where the scene is plane, the plane being tilted at an angle δ, defined as the angle between the scene plane and a horizontal line, and 6 is between 30° and 50°.

11. The method of claim 1 where the angle δ is more than or equal to 35°.

12. The method according to claim 1 where the angle δ is less than or equal to 45°.

13. A system for assessing objectively a refractive characteristic and/or a lag characteristic of one eye of a patient according to a method including: a) positioning the patient's head in a reading position where an object to be read is situated between 25 to 50 cm from the eye or from spectacles plane of the patient and where the patient's head is tiled at an angle β, defined as the angle between the axis of the chest of the patient and patient's head position, where β is between 10° and 40°; b) determining the refractive characteristic and/or the lag characteristic by using a skiascope, the skiascope being arranged to emit a light beam; and wherein the determination of the refractive characteristic is performed when the patient is viewing a scene and where the light beam passes through the scene, where said scene is plane, the plane being tilted at an angle δ, defined as the angle between the scene plane and a horizontal line, and δ is between 30° and 50°, the system comprising:
   a head support arranged to position the patient's head in a reading position so that the patient's head is tilted at an angle β, defined as the angle between the axis of the chest of the patient and the patient's head position, where β is between 10° and 40°;
   a skiascope used to assess the refractive and/or lag characteristic of the eye, the skiascope being arranged to emit a light beam;
   an inclined scene support supporting a viewing scene arranged to be substantially perpendicular to the patient's viewing direction and arranged to be situated between 25 to 50 cm from the eye or from spectacles plane of the patient, where the light beam of the skiascope can pass through said scene and where said scene is plane, the plane being tilted of at an angle δ defined as the angle between the scene plane and a horizontal line, and δ is between 30° and 50°;

a mirror situated on a light path between the skiascope and the patient's head.

14. The system according to claim 13 where the mirror is horizontal.

* * * * *